United States Patent [19]

Orlosky

[11] Patent Number: 4,834,749

[45] Date of Patent: May 30, 1989

[54] HAPTIC ATTACHMENT METHOD AND ASSEMBLY

[75] Inventor: Henry A. Orlosky, Irvine, Calif.

[73] Assignee: Texceed Corporation, Irvine, Calif.

[21] Appl. No.: 137,890

[22] Filed: Dec. 24, 1987

[51] Int. Cl.$^4$ .................... A61F 2/16; B21D 39/00; B29D 11/00

[52] U.S. Cl. .................... 623/6; 29/522.1; 264/1.4; 264/1.7

[58] Field of Search .................... 623/6; 264/1.1, 1.4, 264/1.7; 29/522 R

[56] References Cited

U.S. PATENT DOCUMENTS

| | | | |
|---|---|---|---|
| 3,994,027 | 11/1976 | Jensen et al. | 623/6 |
| 3,996,626 | 12/1976 | Richards et al. | 623/6 |
| 4,104,339 | 8/1978 | Fetz et al. | 264/1.1 |
| 4,242,761 | 1/1981 | Chase et al. | 623/6 |
| 4,485,498 | 12/1984 | Gimbel | 623/6 |
| 4,585,454 | 4/1986 | Fabricant | 623/6 |
| 4,588,405 | 5/1986 | Knolle | 623/6 |
| 4,615,701 | 10/1986 | Woods | 623/6 |
| 4,617,023 | 10/1986 | Peyman | 623/6 |
| 4,629,461 | 12/1986 | Clayman et al. | 623/6 |
| 4,642,114 | 2/1987 | Rosa | 623/6 |

FOREIGN PATENT DOCUMENTS 208546  1/1987  European Pat. Off. ............... 623/6

OTHER PUBLICATIONS

Advertisement—Eur. J. Implant and Refractory Surgery 4 (5) pp. 26 248–249, rear cover (1987).
Advertisement—Contact and Intraocular Lens Medical J. 8 (3) 146 (1982).
Advertisement—Ibid., 8 (4) 16 (1982).
Advertisement—K/Cataract & Refractove Sirgeru 16 (3) omsode front cover, p. 260 (1987).
Advertisement—J. Ocular Therapy & Surgery 3 (1) pp. 2,6, rear cover (1984).
Advertisement—Ibid., 3 (2) pp. 57–58, rear cover.
Advertisement—Ophthamology Times 12 (24) 5 (1987).
Advertisement—Ibid., 13 (7) 2 (1988).
Advertisement—J. Amer. Intraocular Implant-Soc. 11 (6) pp. 538,546,548–549, 630–631 (1985).
Advertisement—Australian and New Zealand J. Ophthamology 14 (1) pp. 4, 40, 76 (1986).
Article-A buying guide for intraocular lenses compiled by Opthalmalogy Times.
Article—A capsule amrket survey; Arch Opthalmol 104 Dec. 1769.

*Primary Examiner*—Ronald L. Frinks
*Attorney, Agent, or Firm*—Lyon & Lyon

[57] ABSTRACT

An improved method and assembly for attaching haptics to intraocular lenses. Method and assembly rely on shaping the attachment ends of plastic or metal haptics so that when inserted into openings in the lens, the haptics are firmly secured to the lens by constraining mechanical forces which arise from an added element, by molding or forming the constraint in situ using an external energy source to melt material of the haptic, or by bending a metal haptic to a holding shape. Melting of lens material is not required for this fastening method or assembly nor is wetting of haptic surfaces by material of the lens necessary.

20 Claims, 3 Drawing Sheets

HAPTIC ATTACHMENT METHOD AND ASSEMBLY

BACKGROUND OF THE INVENTION

This invention relates to an improved attachment method and assembly for securing haptics to intraocular lenses. At the present time haptics, which are used to center and support intraocular lenses within the eye, are attached to the lenses by a variety of mechanical means. In one method peripheral material integral with the lens is carefully machined into supports of the desired shape and dimensions. This method is inherently expensive and is subject to breakage of the relatively brittle supports.

U.S. Pat. Nos. 4,615,701, 4,617,023, and 4,585,454 describe several intraocular lens designs wherein haptics are secured with currently available techniques. U.S. Pat. No. 3,996,626 discloses a variety of haptic designs and describes a method of securing haptics by means of a beading technique involving the melting of the end of a metal haptic and then securing the haptic to the lens by the forces generated by the displacement of lens material; it does not appear to take into account the differences in expansion coefficients between the lens material and the metal. U.S. Pat. No. 4,242,761 teaches the use of threaded bores into which haptic filaments can be expanded by force or heat; however, the method can cause foreign material to be trapped between the threads and the haptic only to be released later after implantation. U.S. Pat. No. 3,994,027 describes another method for anchoring metal haptics by heating the haptics ohmically and then pressing them into the lens body. This patent also appears to ignore the problems of bonding dissimilar materials and the differences in thermal expansion between the haptic and the lens.

Figure 1A:
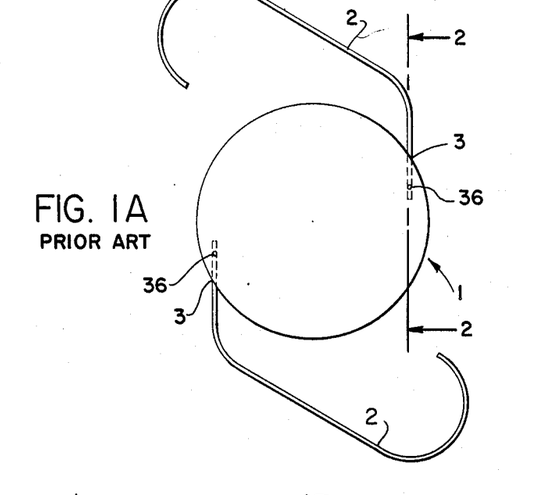
FIG. 1A is a plan view of a representative form of intraocular lens and haptic assembly typical of prior art structures looking at the convex side showing the haptics anchored to the lens.
Figure 1B:
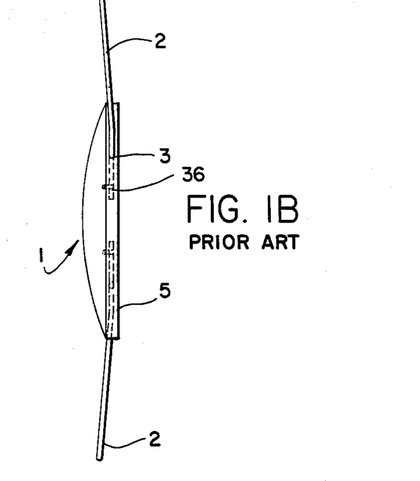
FIG. 1B is an edge view of the intraocular lens of FIG. 1 showing the haptics emerging from the edge of the lens.
Figure 2A:
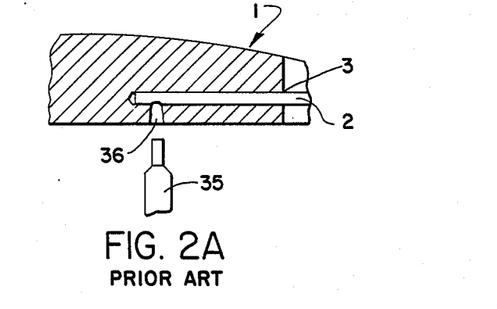
FIG. 2A is an enlarged partial view along line 2—2 of FIG. 1A showing a prior art method of fusing a haptic to an intraocular lens with a heated point.
Figure 2B:
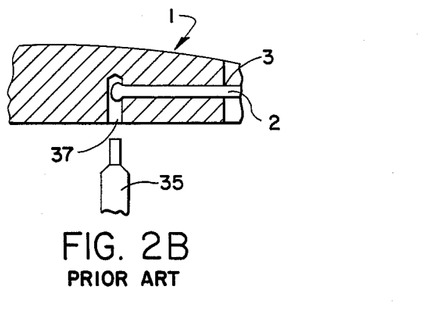
FIG. 2B is an enlarged partial view as in FIG. 2A showing a second prior art method for fastening a haptic to an intraocular lens by enlarging the end of a haptic by a heated point.

Similarly, U.S. Pat. No. 4,104,339 describes a method whereby heated wires or haptics are pressed into the lens body by melting the lens material thereby wetting the heated wire to form a bond between the wire and the lens. The patent also describes the use of a heated point to melt the lens material to hold either a metal or plastic haptic which has been inserted into a chordal hole in the lens and depends only on the melting of the lens material for the fusing operation. U.S. Pat. No. 4,588,405 discloses a method in which a plastic haptic is inserted into a hole in the periphery of the lens and then enlarged at the inner end by melting the haptic by means of a heated rod inserted into a blind hole intersecting the chordal opening. While this method insures that the haptic will not pull out of the hole, it does little to prevent rotation of the haptic within the hole since the melted material neither appears to conform to the walls of the hole nor does it wet the enclosing walls. For reference, FIGS. 1A and 1B show a typical, complete intraocular lens structure with two haptics representative of the prior art. While only two haptics have been shown in the interest of clarity, it is recognized that other numbers and shapes of supports or haptics have also been used. Two illustrations of prior art methods for fastening haptics are shown in FIGS. 2A and 2B. In FIG. 2A, heated point 35 is brought to bear onto the planar side of thermoplastic lens 1 so that lens material 36 is melted, thereby fusing haptic 2 to the lens. In FIG. 2B heated point 35, inserted into hole 37, contacts the end of haptic 2 so as to enlarge the end of the haptic by melting, thereby preventing withdrawal of the haptic, but since the haptic material does not appear to fill cavity 37, the haptic may still rotate. Regardless of which of the above methods is used, each lens and haptic assembly is expected to withstand a pull force of at least 50 grams in the direction of the haptic, and, of course, the generation of asperities which might cause eye irritation must be carefully avoided.

In the majority of examples of prior art, haptics are inserted into holes oriented axially or chordally in the intraocular lens body and anchored by the application of heat or mechanical force in combination with perhaps ultrasonic energy to facilitate joining of the parts. However, in all of the foregoing examples known to the inventor, each suffers from one or more defects such as the need to polish the intraocular lens surface after the fastening operation, the possibility of entrapping foreign material which could cause eye irritation and the possibility of excessively distorting the lens mechanically or thermally. In addition, while many of the extant configurations may resist a pull test of 50 grams, or may resist relatively strong twisting forces, they are not known to have both capabilities simultaneously.

It is therefore an object of this invention to produce an improved attachment method and assembly for attaching haptics to intraocular lenses.

A further object of this invention is to produce an attachment method and assembly for anchoring haptics to intraocular lenses whereby pull test strengths well in excess of the required 50 grams is achieved simultaneously with a high torque resistance, thereby increasing the reliability of the lens assembly.

Another object of this invention is to produce an attachment method which minimizes the possibility of optical distortion by neither melting nor overly stressing the lens material.

It is a still further object of this invention to provide the foresaid objectives in a viable manufacturing mode capable of high production yields in order to minimize the cost of fabrication of intraocular lens implants.

SUMMARY OF THE INVENTION

An improved attachment method and assembly for fastening haptics to intraocular lens implants have been invented. The new attachment method and assembly and their variations eliminate possible problems associated with melting the lens material and optical distortion caused by excessive mechanical stresses in the lens. In the preferred embodiment a spherical plug secures a thermoplastic or a metal haptic to the lens by mechanical constraint so that the haptic has a high resistance both to axial pull and to torque about the axis of the haptic. In two modifications of the improved method, the plug which secures the haptic is formed in situ from material of the haptic itself using a non-contacting, focussed source of energy. Neither of the modified methods depends upon melting of the lens or wetting of the haptic material by the molten lens material. Rather, the fastening of the haptic is accomplished by a firm but non-stressing mechanical holding force in conjunction with the configuration of the attachment end of the haptic. In a third modification, the attachment slot in the lens body is changed to provide another reliable means for securing metal haptics.

DESCRIPTION OF THE PREFERRED EMBODIMENT

Figure 3A:
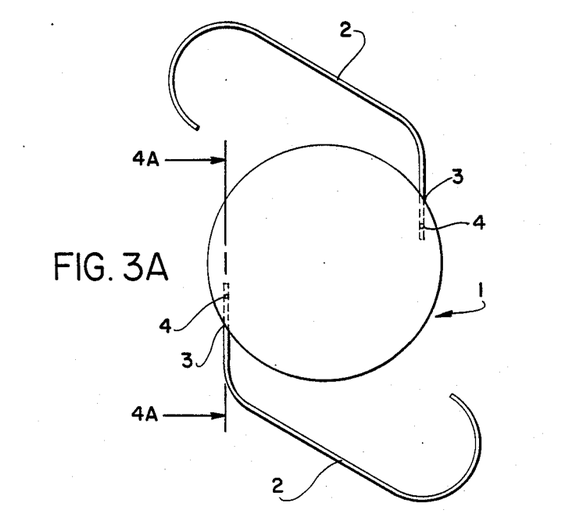
FIG. 3A is a plan view of an intraocular lens and haptic assembly structure according to the present invention looking at the convex side showing the haptics anchored to the lens.
Figure 3B:
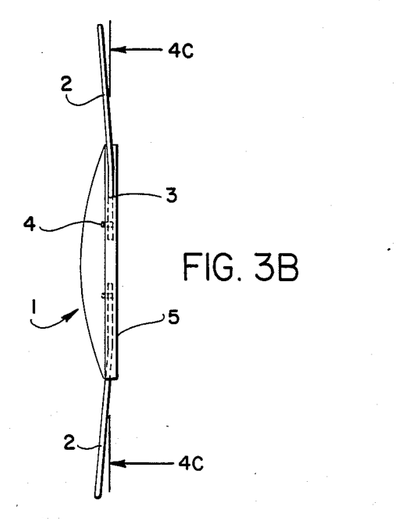
FIG. 3B is an edge view of the intraocular lens of FIG. 3A showing the haptics emerging from the edge of the lens.

The invention as herein disclosed relates to an improved intraocular lens attachment method and assembly and variations thereof for anchoring haptics of various shapes into intraocular lens implants of numerous designs and therefore applies to the interface region encompassing the haptic and the lens. All of the lens bodies now used for lens implants are made of an optical grade of thermoplastic like polymethyl methacrylate which is well tolerated by the body. The preferred embodiment utilizes mechanical interference fits of shaped materials to effect the anchoring of either thermoplastic or metal haptics. With slight modifications, the molding of shaped materials in situ in cavities in the intraocular lenses will anchor thermoplastic haptics securely. A further modification provides for another way to anchor metal haptics. Referring to FIGS. 3A and 3B, a complete intraocular lens for the present invention is shown in plan and side views. In this case also only two haptics are shown for the sake of clarity but any other number of supports or haptics may be used. As shown, FIGS. 3A and 3B are superficially similar to the prior art. However, the differences between the prior art and the present invention are found at the attachment point of the haptic to the lens; the improved method and structure for producing the attachment results in a highly reliable lens assembly suitable to high yield production.

Figures 4A, 4B, 4C, 5, 6, 7A, 7B, 7C, 8A:
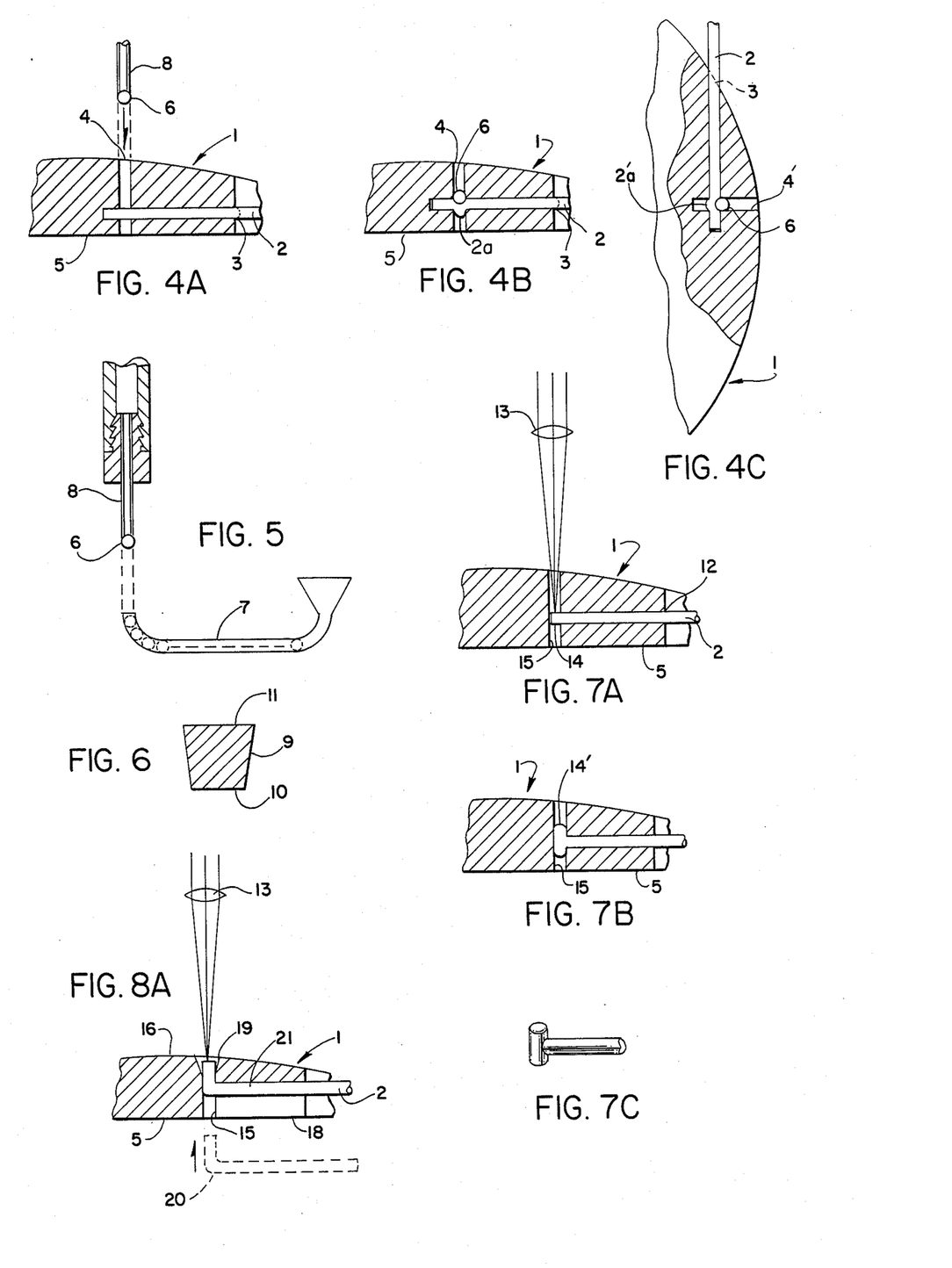
FIG. 4A is an enlarged, partial view along line 4A—4A in FIG. 3A showing a haptic in position to be secured in place by a sphere centered over the anchoring position by a vacuum cannula according to the present invention.
FIG. 4B is the same view as in FIG. 4A showing the haptic secured by a spherical plug.
FIG. 4C is an enlarged, partial plan view of an alternative hole configuration along line 4C—4C of FIG. 3B.
FIG. 5 shows a vacuum cannula picking up a spherical plug from a supply means for transport to the lens.
FIG. 6 is a cross section of an alternate shape of plug for securing the haptic.
FIG. 7A is a view similar to FIG. 4A showing the start of the operation to form a securing plug for the haptic in situ using a focussed energy source.
FIG. 7B is the same view as FIG. 7A showing the haptic securely held in place by the formed end.
FIG. 7C is an enlarged perspective view of the formed haptic removed from the intraocular lens showing more clearly the molded "tee" shaped end.
FIG. 8A is similar to FIG. 7A showing the start of the operation forming a modified securing plug for the haptic in situ using the same method as in FIGS. 7A thru 7C.

The method of the preferred embodiment can be understood by referring to FIGS. 4A and 4B which show enlarged views of the attachment region. Haptic 2 is inserted into a chordal opening 3 of intraocular lens 1 for a distance of three to four haptic diameters beyond the edge of a transverse hole 4 which intersects opening 3 axially. Transverse hole 4 is substantially normal to surface 5 of intraocular lens 1 but can be at any convenient angle thereto, up to 15 degrees from the normal for example. Chordal opening 3 may have various cross sectional shapes but it has been found convenient to use round holes. Opening 3 is a round hole of diameter large enough to permit sliding fit of haptic 2 and with a length at least equal to one third the chordal length. The diameter of transverse hole 4 is nominally the same as the diameter of opening 3, and sphere 6 has an optimal diameter between 2 to 10 percent in excess of the diameter of hole 4. When forced into hole 4 to a depth sufficient to deform haptic 2 a distance at least equal to the radius of the haptic, the interference produced by the excess diameter holds the haptic securely. Haptic 2, being so deformed, not only resists axial pull, but because of its acquired crank-shaped form 2a, also resists rotational torque. Sphere 6 is obtained from supply means 7 by vacuum cannula 8 as in FIG. 5 and is transferred to a position over the center line of hole 4 as shown in FIG. 4A. It is then deposited therein and pushed into its final position by cannula 8, thereby securing haptic 2 to intraocular lens 1 as shown in FIG. 4B. Although vacuum cannula 8 provides a reliable way to transport spheres 6 from supply means 7 to hole 4, there are times when a vacuum device would not be convenient. An alternative method, which is still within the scope and spirit of this invention, is to apply an electrical charge or potential to cannula 8 or an electrode of equivalent shape and rely on electrostatic attraction to hold sphere 6 for transporting.

The assembly method as described above has been shown to be a viable means for securing haptics to intraocular lenses. However, it has also been found that the method can be improved by including three additional steps to the process. One is to add a small chamfer or radius to hole 4 to facilitate insertion of sphere 6 into the hole and to prevent the generation of any chips from the otherwise sharp edge of the hole. The second step is to heat the lens to a temperature somewhere between 120 to 165 degrees Fahrenheit. The heating not only expands the diameter of hole 4, but also softens the lens material sufficiently that no excessive strains are produced when the sphere is put into place and allows relaxation of the lens material surrounding the sphere and haptic. This relaxation of stress in the lens material is not sufficient to cause loosening of the fastening but is known to minimize any optical distortion from radiating outward of the fastening region. The actual temperature to be used for the assembly method has been found to depend on the exact formulation of the lens material which usually varies from one plastics manufacturer to another. The third step is to aid the movement of the sphere along the hole 4 by driving either the vacuum cannula or the electrode by an ultrasonic or other vibratory energy source to overcome frictional forces. Hole 4 as shown passes through both surfaces of intraocular lens 1. However, if desired hole 4 may be a blind hole which extends far enough beyond opening 3 to allow sphere 6 to produce the crank-shaped form 2a in haptic 2. Although sphere 6 is shown as being put into lens 1 through the convex side, the method is equally applicable to insertion from the planar side of the lens. The amount of deformation required to anchor haptic 2 securely depends quantitatively on the diameter and material of the haptic and on the diameter of hole 4 with respect to the diameter of sphere 6. For example, hard materials require less deformation than soft materials for the same holding capability. Haptic 2 may be made of thermoplastic filamentary material or metal. Materials with satisfactory mechanical properties for sphere 6 may be selected from a wide variety of materials such as organic and inorganic plastics, ceramics, glass, and metal as long as they meet the criteria of human body compatability and chemical stability. The plastic materials for the plug and haptic can be thermoplastic materials from the classes which include the addition polymers such as polymethyl methacrylate and polystyrene, and the condensation polymers such as polyimides, polycarbonates, polysulfones, polyphenylene, polyphenylene sulfide, polyphenylene oxide, and polymethylpentene. Haptic 2 is normally about 0.13 mm (0.005 inch) in diameter which establishes the size of chordal opening 3 and transverse hole 4; sphere 6 is two to ten percent larger than the diameter of hole 4 thus requiring close dimensional control of the size of the sphere. Maintaining close control of the sphere dimension is not difficult, however, since spheres are available in production quantities in the required materials and size range and are easily classified to a specific size well within required tolerances. Thus, once a set of materials for the haptic and sphere has been selected, proper sizes can be obtained easily from commercial sources, thereby maintaining the required dimensional control for the preferred embodiment in a cost effective manner. The assembly operation of securing the haptic to the lens can then be reproducibly performed with high production yields because the preselection of properly sized components eliminates the need for critical dimensional control at the assembly stage. In the actual assembly operation the lens is held in a micropositioner and haptic 2 and cannula 8 are held by collets, for example, whose positions are also controlled by micropositioners. Such micropositioning apparatus can be custom made or adapted from commercially available equipment but are not considered to be part of this invention.

The mechanical method described above for the preferred embodiment may have some further variations. Features common to the preferred embodiment and the variations described below are the chordal opening and the transverse hole axially intersecting the chordal opening; only slight changes in the shapes or positions of the chordal opening and/or the transverse hole are required to accomplish these minor variations. FIG. 4C illustrates one such variation in which transverse hole 4' is located in the edge of the lens in the same manner as the chordal opening. Except that the plane formed by the axes of chordal opening 3 and transverse hole 4' is now substantially coplanar with the plane of lens 1 rather than perpendicular thereto as in the preferred embodiment, all other features of the preferred embodiment apply equally well here. The modification shown in FIG. 4C may be desirable to permit utilization of assembly machinery which is oriented to handle lenses in the vertical plane. In all of the foregoing embodiments shown in FIGS. 3A through 4C, transverse holes 4 or 4' intersect chordal opening 3 at a distance from the inward end of chordal opening 3 at least several times the cross sectional dimension of the hole. Positioning the intersection at this stated distance insures that adequate holding force will be generated for reliable anchoring of the haptic. Also, as would be apparent to one skilled in the art, the shape of the anchoring or retaining element could include shapes other than spheres. For example a cylindrically shaped plug of unity aspect ratio, shown in cross section in FIG. 6 and similar in shape to a rubber stopper, can replace sphere 6 of the preferred embodiment and be inserted into hole 4 by vacuum cannula 8. The smaller diameter 10 of plug 9 is slightly less than the diameter of hole 4 and is inserted first. The outer diameter 11 is two to ten percent larger than the diameter of hole 4, thus producing a holding force similar to that obtained with the spherical shape. Other shapes which produce a two to ten percent deformation of the wall of hole 4 will produce similar holding capabilities and are within the scope and spirit of this invention.

A holding plug as described above may also be formed in situ for a lens-haptic geometry similar to that of FIG. 4A by melting the end of a thermoplastic plastic haptic with a concentrated energy source such as a laser beam, or a focussed, coherent or incoherent light source or other non-contacting heating means which can penetrate into the transverse hole in the intraocular lens without disturbing the side wall. Since a beam spread of up to 4 degrees will not disturb the sidewall of the transverse hole, the optical focussing requirements are not severe and are easily achievable with commercial energy sources. Examples of focussed energy sources include gas lasers like argon ion, infrared and excimer lasers and solid state lasers like YAG and NdYAG in the one to five watt energy range. The lasers may be pulsed or continuous wave; pulsed sources provide better control of heating rates and are therefore preferred over cw lasers. Either a lens system alone or in conjunction with fiber optics may be used to direct the energy to the haptic being softened.

FIG. 7A illustrates one such modification of the preferred embodiment for forming plugs in situ. By using a non-contacting heating means, haptic material is free to mold itself to the confines of transverse hole 4, without the necessity of welding it to the lens. Thus, the molded plug formed on the end of the haptic partially fills and conforms to the contours of the transverse hole and effectively anchors the haptic. The insulating effect of the gas layer on the sidewall of transverse hole 4 and the short heating time for melting the haptic work together to minimize heat transfer to the lens in contrast to the direct heat transfer occurring when a welding process is used. Chordal opening 12 in intraocular lens 1 slidably contains the haptic 2 and terminates at transverse hole 15. Except for its slightly shorter length, opening 12 is identical to opening 3 of FIG. 4A and hole 15 is identical to hole 4 of FIG. 4A. Focussed energy source 13 is brought to bear on end 14 of haptic 2 simultaneously with the application of an axial force on haptic 2 in the direction of the arrow in FIG. 7A urging the haptic toward hole 15. The axial force can be applied to the haptic through the haptic holder by a steady force and/or be assisted by an ultrasonic or other vibratory energy source to relieve any frictional effects. Haptic 2, being slidably contained in chordal opening 12, now moves in the direction of the applied force as energy source 13 softens end 14 of haptic 2; the softened material moves into the volume of hole 15 and end 14 assumes the shape 14' as shown in FIG. 7B. FIG. 7C which shows haptic 2 removed from lens body 1, is a perspective view illustrating reformed end 14' in idealized form. It can be seen that the end 14' of haptic 2 has been molded to the shape of hole 15 to form a "tee" shape which provides not only an anchor in the axial direction of haptic 2 but, because of the length of molded end 14', provides a firm restoring force against rotation.

Figure 8B:
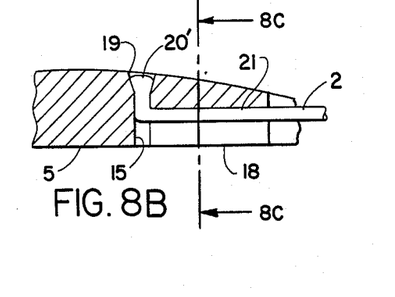
FIG. 8B is the same view as FIG. 8A showing the haptic securely held in place by the modified formed end.
Figure 8C:
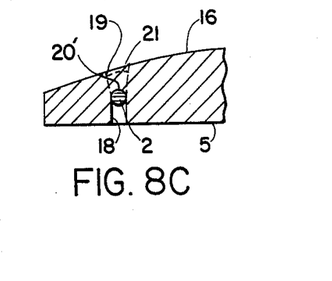
FIG. 8C is a partial cross sectional view taken along line 8C—8C of FIG. 8B showing the slot for accepting the haptic.
Figure 8D:
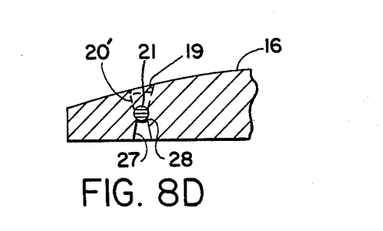
FIG. 8D is a partial cross sectional view taken as in FIG. 8B showing an alternative, keyhole shaped slot for accepting the haptic.
Figure 8E:
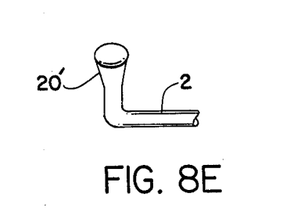
FIG. 8E is an enlarged perspective view of the haptic removed from the intraocular lens showing the conical shape formed by the method of FIG. 8A.

In FIGS. 8A through 8E it can be seen that by modifying the chordal opening from the cylindrically shaped hole 12 of FIG. 7A to a slot 18 and enlarging the outer end of hole 15 into conical hole 19, a second in situ method for securing haptics is possible. Conical hole 19 tapers outwardly to the outer surface 16 of lens body 1 from the inner edge 21 of chordal slot 18; the inner diameter of conical hole 19 is substantially equal to the width of chordal slot 18 and the outer diameter is between 1.15 and 1.30 times the inner diameter. Similar to chordal opening 3 of FIG. 4A, slot 18 is at least as long as one third the length of the chord and of depth at least twenty percent greater than the diameter of the haptic. The attachment end 20 of haptic 2 in FIG. 8A is bent at an angle matching the angle between the axis of hole 15 and inner edge 21 of slot 18, the angle usually being close to 90 degrees. Short end 20 of haptic 2 is cut so that it does not protrude beyond surface 16 of intraocular lens 1 when inserted into slot 18 as shown in FIG. 8A. When energy source 13 heats end 20 of haptic 2, the material of haptic 2 flows and fills conical shape 19 to form plug 20' which effectively secures haptic 2 to intraocular lens 1 both in the axial direction and rotationally as can be seen with reference to FIG. 8B. FIG. 8C is a partial cross sectional view along line 8C—8C of FIG. 8B showing the cross section of slot 18 with haptic 2 in place. Slot 18 in FIG. 8C slidably contains haptic 2 and has parallel sides. The slot may also have a cross section as in FIG. 8D wherein it is given a keyhole shape 27 such that narrow dimension 28 of the keyhole is slightly less than the diameter of haptic 2. In this case haptic 2 will be held along its length in the slot so as to provide a holding means for the haptic during the plug forming process; i.e. it is self fixturing. FIG. 8E shows the shape of end 20' of haptic 2 after forming as it would appear if removed from the body of lens 1. Although FIGS. 8A through 8D show slot 18 in the planar side of the lens, if it should be otherwise desirable, slot 18 may equally well be placed in the convex side of the lens.

Figure 9A:
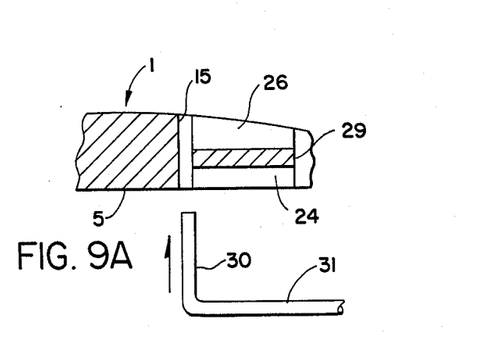
FIG. 9A illustrates a modification of the slot shown in FIG. 8A to allow the securing of metal wire haptics to the intraocular lens and showing a wire haptic in position prior to insertion into the lens.
Figure 9B:
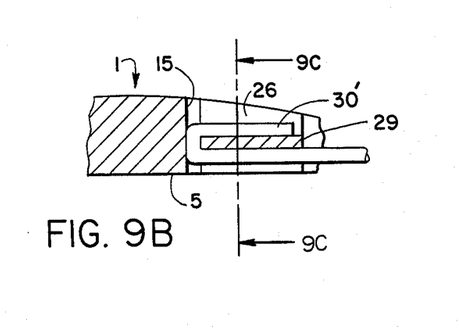
FIG. 9B shows the metal haptic securely attached to the intraocular lens.
Figure 9C:
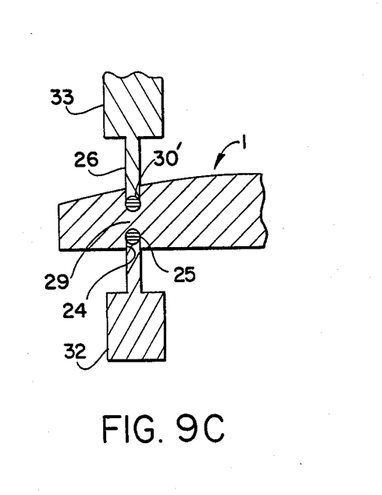
FIG. 9C is a partial cross sectional view taken along line 9C—9C of FIG. 9B showing the forming tools used for securing the metal haptic to the intraocular lens.

A further moderate, progressive variation of the preferred embodiment results in a second method for anchoring metal haptics. By modifying chordal opening 12 of FIG. 7A successively into a slot 18 as shown in FIG. 8A and then into a double slot of sections 24 and 26 as shown in FIG. 9A, metal haptics can be attached to an intraocular lens by a mechanical holding process. By adding the second slot 26 in the same plane as slot 24, but at the other end of hole 15, chordal opening 12 becomes a slot with webb 29 between them, as shown in FIGS. 9A and 9B. The same dimensional considerations apply to slots 24 and 26 of FIG. 9A as apply to slot 18 of FIG. 8A in that they are at least as long as one third the chordal length and at least twenty percent deeper than the diameter of the haptic. When slots 24 and 26 are made, the material of the lens remaining between them forms webb 29 of thickness substantially equal to the diameter of the haptic material. Thus with this slot configuration it is possible to anchor haptics made of metals such as tantalum, platinum, iridium, titanium and their alloys which are tolerated by the body. The lens material between slots 24 and 26 forms webb 29 which serves as the anchor for the metal haptic. End 30 of metal haptic 31 is bent into a form similar to that of end 20 of haptic 2 in FIG. 8A, but end 30 is about twice as long as end 20. After insertion of end 30 of haptic 31 into hole 15, end 30 is bent back into contact with webb 29 at the bottom of slot 26, becoming 30'. Since the metal of haptic 31 is so much stronger than the plastic of intraocular lens 1, and since the lens is so light in weight, the wire hook so formed will very easily hold the lens securely. FIG. 9C is a partial cross section along line 9C—9C of FIG. 9B showing how haptic 31 and haptic end 30' lie in their respective slots 24 and 26 on either side of webb 29 after bending. In the bending process anvil 32 supports haptic 31 as plunger 33 bends haptic end 30; the anvil and plunger are illustrative of tooling which will accomplish the forming operation. Just as in the foregoing embodiments of the invention, haptic 31 cannot move axially or rotatively with respect to the lens 1 because the geometry of the formed wire hook prevents such motion.

The cross sections of the haptics, the holes, and the chordal openings in the preferred embodiments are circular because commonly available haptic materials are of round cross section. However, other haptic cross sectional shapes, e.g. square or rectangular, are readily adaptable to the methods of this invention should such shapes become commercially available and are well within the scope and intent of this invention.

What is claimed is:
1. A method for securing a haptic to an intraocular lens comprising the steps:
  making a chordal opening in the form of a hole at the edge of said intraocular lens and penetrating said lens a distance of at least one third the length of the chord, said opening being nominally parallel to the plane of said lens;
  forming a transverse hole substantially intersecting said chordal opening axially at its inward end at a point at least several times the major dimension of said hole from said inward end of said chordal opening and with said transverse hole being at a angle to said chordal opening;

inserting the shank of said haptic substantially into said chordal opening;

transporting a plug of major dimension two to ten percent larger than the major dimension of said transverse hole to said transverse hole from a supply means; and, inserting said plug into said transverse hole and moving said plug inwardly of the lens so as to contact and deform said haptic into said transverse hole a distance at least equal to one half the average cross section of said haptic, thereby securely fastening said haptic to said lens by virtue of the interference fit between said plug and said lens.

2. A method for securing a haptic to an intraocular lens as in claim 1 wherein the materials of said haptic and said plug are thermoplastic materials from the classes which include the addition polymers polymethyl methacrylate and polystyrene, and the condensation polymers polyimides, polycarbonates, polysulfones, polyphenylene, polyphenylene sulfide, polyphenylene oxide, and polymethylpentene.

3. A method for securing a haptic to an intraocular lens comprising the steps:

making a chordal opening in the form of a round hole at the edge of said intraocular lens and penetrating said lens a distance of at least one third the length of the chord, said opening being nominally parallel to the plane of said lens;

forming a transverse hole through said lens chamferred at both ends and of diameter equal to and intersecting said chordal opening axially at its inward end at a point at least several times the diameter of said hole from said inward end of said chordal opening and with said transverse hole being nominally perpendicular to said chordal opening and to the plane of said intraocular lens;

inserting the shank of said haptic fully into said opening;

transporting a spherical plug of diameter two to ten percent larger than the diameter of said transverse hole to the mouth of said transverse hole from a supply means using a vacuum cannula small enough to slide into said hole without constraint;

heating said lens to a temperature between 120 and 165 degrees Fahrenheit; and, inserting said spherical plug into said transverse hole and moving said plug inwardly of the lens so as to contact and deform said haptic into said transverse hole a distance at least equal to one half the diameter of said haptic, thereby securely fastening said haptic to said lens by virtue of the interference fit between said spherical plug and said lens.

4. A method for securing a haptic to an intraocular lens as in claim 3 wherein said transverse hole intersects said chordal opening axially at its inward end at a point at least several times the diameter of said hole from said inward end of said chordal opening and with said transverse hole being nominally perpendicular to said chordal opening and nominally parallel to the plane of said intraocular lens.

5. A method for securing a haptic to an intraocular lens as in claim 3 wherein said plug is transported to the mouth of said transverse opening from a supply means by a charged electrode of dimensions comparable to said vacuum cannula, said electrode holding said plug by electrostatic attraction.

6. A method for securing a haptic to an intraocular lens as in claim 3 wherein said plug is a tapered cylinder of unity aspect ratio with a large end and a small end and wherein said large end is two to ten percent larger in diameter than said transverse hole and said small end is two to ten percent smaller than the diameter of said hole diameter.

7. A method for securing a haptic to an intraocular lens as in claim 3 wherein said vacuum cannula may be driven by a vibratory energy source.

8. A method for securing a haptic to an intraocular lens as in claim 5 wherein said electrode may be driven by a vibratory energy source.

9. A method for securing a thermoplastic haptic to an intraocular lens comprising the steps:

making a chordal opening in the form of a round hole at the edge of said intraocular lens and penetrating said lens a distance of at least one third the length of the chord, said opening being nominally parallel to the plane of said lens;

making a transverse hole through said intraocular lens, of diameter equal to and intersecting said chordal opening axially at its inward end to form a "tee" shaped cavity, said transverse hole being nominally perpendicular to said chordal opening and to the plane of said intraocular lens;

inserting the shank of said haptic fully into said opening to position the inner end of said shank in said transverse hole;

urging said haptic toward said transverse hole as said inner end of said haptic is heated and softened by a non-contacting heating source centered on the axis of said transverse hole; and, forming a "tee" shaped molded plug in the volume of said transverse hole as the heated inner end of said haptic flows, thereby anchoring said haptic firmly in place.

10. A method for securing a thermoplastic haptic to an intraocular lens as in claim 9 wherein said haptic is urged toward said transverse hole by a vibratory force.

11. A method for securing a thermoplastic haptic to an intraocular lens as in claim 9 wherein said non-contacting thermal source is a laser beam.

12. A method for securing a thermoplastic haptic to an intraocular lens as in claim 9 wherein said non-contacting thermal source is a focussed, non-coherent light source.

13. A method for securing a thermoplastic haptic to an intraocular lens comprising the steps:

making a chordal opening as a slot in a first side of said lens for a distance of at least one third the length of the chord, said slot having a width so as to allow slidable entry of said haptic, having a depth at least twenty percent greater then the diameter of said haptic, and having a bottom surface nominally parallel to the plane of said lens;

making a conical hole in a second side of said lens, the axis of said conical hole being nominally perpendicular to the plane of said lens and intersecting axially the inward end of said slot and communicating fully therewith, said conical hole having an inner diameter matching the width of said slot and tapering outward toward said second side of the lens to a diameter 1.15 to 1.30 times said inner diameter;

preforming the shank of said haptic to have a short end and a long end, said short end and said long end being at an angle matching the angle between the axes of said slot and said conical hole and having the terminus of said short end of said shank long enough to reach but not penetrate said second side of said lens;

inserting said short end of said haptic into said conical hole and said slot: and, heating said short end of said haptic projecting into said conical hole by a non-contacting energy source causing the haptic material to flow and be molded in situ to the shape of said conical hole, thereby securely anchoring said haptic to said lens.

14. A method for securing a metal haptic to an intraocular lens comprising the steps:

making a first chordal opening as a slot in a first side of said lens for a distance of at least one third the length of the chord, having a width to allow said haptic slidable entry and having a depth at least twenty percent greater than the diameter of said haptic;

making a second chordal opening as a slot in a second side of said lens for the same distance as said first chordal opening and coplanar therewith, having a width to allow said haptic slidable entry and having a depth at least twenty percent greater than the diameter of said haptic and separated from said first first chordal opening by a webb of material of said lens of thickness substantially equal to the diameter of said haptic;

making a transverse hole of diameter at least equal to the diameter of said haptic communicating fully with the inner end of said first slot and with the inner end of said second slot;

preforming the shank of said metal haptic so as to have a short end and a long end substantially at ninety degrees so that said short end of said haptic is no longer than the length of said second chordal opening;

inserting said bent portion of said metal haptic into said first chordal opening and through said transverse hole; and, bending said short end of said haptic a second time so that the remaining part of said short end lies in said second chordal opening parallel to and against said webb, thereby securing said haptic to said lens.

15. An intraocular lens and haptic assembly comprising:

an intraocular lens;

a chordal opening in the form of a hole at the edge of said intraocular lens and penetrating said lens a distance of at least one third the length of the chord, said opening being nominally parallel to the plane of said lens;

a transverse hole substantially intersecting said chordal opening axially at its inward end at a distance at least several times the cross sectional dimension of said hole from said inward end of said chordal opening and with said transverse hole being at an angle to said chordal opening;

a haptic inserted substantially into said chordal opening and passing beyond said transverse hole; and, a plug of major dimension two to ten percent larger than the major cross sectional dimension of said transverse hole, said plug being inserted into said transverse hole so as to contact and deform said haptic into said transverse hole a distance at least equal to one half the average cross section of said haptic, thereby securely fastening said haptic to said lens by virtue of the interference fit between said plug and said lens.

16. An intraocular lens and haptic assembly comprising:

an intraocular lens;

a chordal opening in the form of a round hole at the edge of said intraocular lens and penetrating said lens a distance of at least one third the length of the chord, said chordal opening being nominally parallel to the plane of said lens; a transverse hole substantially intersecting said chordal opening axially at a distance at least several diameters of said transverse hole from the inward end of said chordal opening and with said transverse hole being substantially perpendicular to said chordal opening and to the plane of said lens;

a haptic inserted fully into said chordal opening; and, a spherical plug having a diameter two to ten percent larger than the diameter of said transverse opening and inserted therein so as to contact and deform said haptic into said transverse hole a distance at least equal to one half the diameter of said haptic, thereby securely fastening said haptic to said lens by virtue of the interference fit between said spherical plug and said lens.

17. An intraocular lens and haptic assembly in claim 16 wherein said haptic is secured to said intraocular lens by a tapered cylindrical plug of unity aspect ratio with a large end and a small end wherein said large end is two to ten percent larger than the diameter of said transverse hole and said small end is two to ten percent smaller than the diameter of said transverse hole.

18. An intraocular lens and haptic assembly comprising:

an intraocular lens;

a thermoplastic haptic;

a chordal opening as a hole at the edge of said intraocular lens and penetrating said lens a distance of at least one third the length of the chord and of size so as to slidably retain said haptic, said chordal opening being nominally parallel to the plane of said lens;

a transverse hole through said intraocular lens, being of a size at least equal to the size of said chordal opening, and nominally perpendicular to the plane of said intraocular lens, intersecting said chordal opening axially at the inner end and communicating fully therewith to form a "tee" shaped cavity;

said "tee" shaped cavity being filled with haptic material as said haptic is melted in situ by a non-contacting energy source focussed on the end of said haptic slidably retained in said chordal opening as said haptic is urged toward said tee shaped cavity, said melted material forming a "tee" shaped plug integral with said haptic, thereby securely fastening said haptic to said lens.

19. An intraocular lens and haptic assembly comprising:

an intraocular lens;

a thermoplastic haptic;

a chordal opening as a slot in a first side of said lens for a distance of at least one third the length of the chord, having a width so as to allow slidable entry of said haptic, having a depth at least twenty percent greater than the diameter of said haptic, and having a bottom surface nominally parallel to the plane of said lens;

a conical hole in a second side of said lens, of inner diameter at least equal to the width of said slot and taperedly expanded toward said second side of said lens to between 1.15 and 1.30 times said inner diameter, the axis of said conical hole being nominally perpendicular to the plane of said lens and intersecting axially the inward end of said slot and communicating fully therewith;

a shank of said haptic preformed to have a short end and a long end, said short end formed to an angle matching the angle between the axes of said slot and said conical hole and inserted therein, the terminus of said short end of said shank long enough to reach but not penetrate said second side of said lens; and, a retaining plug formed integrally with said short end of said haptic when said terminus is melted in situ by a non-contacting, focussed energy source, thereby securely anchoring said haptic to said lens.

20. An intraocular lens and haptic assembly comprising:

an intraocular lens;

a metal haptic;

a first chordal opening as a slot in a first side of said lens extending into said lens at least one third the length of the chord, having a width to allow said haptic slidable entry, having a depth at least twenty percent greater than the diameter of said haptic, and having a bottom surface nominally parallel to the plane of said lens;

a second chordal opening as a slot in a second side of said lens coplanar with said first slot, having a width to allow said haptic slidable entry, having a depth at least twenty percent greater than the diameter of said haptic, having a bottom surface parallel to the plane of said lens and separated from said first chordal opening by a webb of material of said lens, said webb having a thickness substantially equal to the diameter of said haptic;

a transverse hole of diameter at least equal to the diameter of said haptic communicating fully with the inner end of said first slot and with the inner end of said second slot;

a shank of said metal haptic preformed to have a short end and a long end, said short end bent at a right angle to said long end, said short end being no longer than the length of said second chordal opening, said short end of said haptic being inserted into first chordal opening and through said transverse hole; and, a holding hook around said webb formed by a second bend of said short end such that said short end lies in said second chordal opening parallel to and against said webb, thereby securing said haptic to said lens.

* * * * *